US006585698B1

(12) United States Patent
Packman et al.

(10) Patent No.: US 6,585,698 B1
(45) Date of Patent: Jul. 1, 2003

(54) ELECTRONIC MEDICAL DELIVERY PEN HAVING A MULTIFUNCTION ACTUATOR

(75) Inventors: Jay D. Packman, Tuxedo, NY (US); John E. Burbank, III, Ridgefield, CT (US); Antonio A. Bendek, Vernon, NJ (US); Robert C. Uschold, Monroe, NY (US)

(73) Assignee: Becton, Dickinson & Company, Franklin Lakes, NJ (US)

( * ) Notice: Subject to any disclaimer, the term of this patent is extended or adjusted under 35 U.S.C. 154(b) by 0 days.

(21) Appl. No.: 09/432,041

(22) Filed: Nov. 1, 1999

(51) Int. Cl.[7] ............................................... A61M 5/00
(52) U.S. Cl. ........................ 604/207; 604/211; 604/232
(58) Field of Search .................................. 604/181, 182, 604/186, 187, 207, 208, 211, 224, 228, 232, 65, 67, 218; 128/DIG. 12–13

(56) References Cited

U.S. PATENT DOCUMENTS

| 4,950,246 A | * | 8/1990 | Muller |
| 4,978,335 A | * | 12/1990 | Arthur, III |
| 5,593,390 A | * | 1/1997 | Castellano et al. |
| 5,820,602 A | * | 10/1998 | Kovelman et al. |

* cited by examiner

Primary Examiner—Brian L. Casler
Assistant Examiner—LoAn H. Thanh
(74) Attorney, Agent, or Firm—Alan W. Fiedler (57) ABSTRACT

A medication delivery pen includes a housing having opposing proximal and distal ends. An actuator is disposed in the proximal end of the housing for setting and administering a dosage of medication. The pen also includes a medication-containing cartridge assembly having a cartridge with a pierceably sealed distal end, an open proximal end removably attachable to the distal end of the housing, and a piston in sliding fluid tight engagement within the cartridge. A drive mechanism is coupled between the actuator and the cartridge to exert an axial force on the piston to inject the set dosage of medication. The actuator triggers the drive mechanism to administer the injection of medication held in the cartridge. A processor is coupled to the actuator to determine a value equal to the dosage set by the actuator. A memory device is coupled to the processor to store at least the dosage value determined by the processor. A display is located on the housing and coupled to the processor for displaying information provided by the processor. In a first state the actuator engages with the drive mechanism to deliver the medication and in a second state is disengaged from the drive mechanism. In its second state, the actuator serves as a user adjustable input for changing and setting mode parameters of at least one preselected mode of the pen.

20 Claims, 7 Drawing Sheets

ELECTRONIC MEDICAL DELIVERY PEN HAVING A MULTIFUNCTION ACTUATOR

BACKGROUND OF THE INVENTION

1. Field of the Invention

The subject invention relates to an improved electronic medication delivery pen.

2. Description of Related Art

Home diabetes therapy requires the patient to carry out a prescribed regimen that involves self-testing blood glucose levels and administering an appropriate dose of insulin. Insulin has traditionally been injected by a hypodermic syringe, which suffers from numerous drawbacks. For example, syringes are not preloaded with medication, requiring the user to carry a separate medical vial. Syringes also require a degree of dexterity and sufficient visual acuity on the part of the patient to line up the needle of the syringe with the rubber septum on the medical vial and to ensure that the syringe is loaded with the proper dosage. As a result, unintentional needle pricks commonly occur.

To overcome the drawbacks of syringes, medication delivery pens have been developed, which facilitate the self-administration of medication such as insulin. Such delivery pens use prepackaged insulin and may be used repeatedly until the medication is exhausted. Mechanical and electronic pens are available. Electronic pens incorporate electronic circuitry that sets and/or indicates the appropriate dosage of insulin and stores data for subsequent downloading such as the time, date, amount of medication injected, etc.

While electronic pens that mechanically simplify the device have been proposed, it has been found that there remains a need for additional features and improvements that further utilize the electronic capabilities of the pen. For example, it would be desirable to automatically determine the amount of insulin that remains in a cartridge from which one or more dosages of medication have been delivered. Likewise, it would be desirable to automatically determine the size of the cartridge that is installed in the pen as well as the type of medication contained in the cartridge, thus allowing many different types of cartridges to be used in a single pen while reducing the likelihood of user error resulting from misidentifying the cartridge or manually entering incorrect information into the pen.

SUMMARY OF THE INVENTION

The subject invention relates to an electronic medication delivery pen in which the value of different modes such as time and date modes are changed by the actuator when the actuator is disengaged from the drive mechanism of the pen.

In accordance with the present invention, a medication delivery pen includes a housing having opposing proximal and distal ends. An actuator is disposed in the proximal end of the housing for setting and administering a dosage of medication. The pen also includes a medication-containing cartridge assembly having a cartridge with a pierceably sealed distal end, an open proximal end removably attachable to the distal end of the housing, and a piston in sliding fluid tight engagement within the cartridge. A drive mechanism is coupled between the actuator and the cartridge to exert an axial force on the piston to inject the set dosage of medication. The actuator triggers the drive mechanism to administer the injection of medication held in the cartridge. A processor is coupled to the actuator to determine a value equal to the dosage set by the actuator. A memory device is coupled to the processor to store at least the dosage value determined by the processor. A display is located on the housing and coupled to the processor for displaying information provided by the processor. In a first state the actuator engages with the drive mechanism to deliver the medication and in a second state is disengaged from the drive mechanism. In its second state, the actuator serves as a user adjustable input for changing and setting mode parameters of at least one preselected mode of the pen.

In some embodiments of the invention the actuator includes a rotatable knob for setting the dosage of medication. The rotatable knob also serves as the user adjustable input when the actuator is in the second state. The rotatable knob may be rotated when in the second state for changing and setting the mode parameters. Other user-inputs that may be provided include a user-activatable mode button located on the housing for selecting the preselected mode of the pen from among multiple modes such as a time and date mode, and an eject button for selectively alternating between the first and second states of the actuator.

In accordance with one aspect of the invention, the medication delivery pen also includes a sensor coupled to the processor for detecting status information pertaining to the drive mechanism to determine a quantity of medication remaining in the cartridge. Such status information may include, for example, the linear position of a leadscrew that forms part of the drive mechanism.

In accordance with another aspect of the invention, the cartridge has an encoded portion which identifies at least one characteristic of the cartridge. A sensor is coupled to the processor for detecting the encoded portion of the cartridge so that the processor can determine the corresponding characteristic of the cartridge. The characteristic of the cartridge that is determined from the encoded portion may be the type of medication in the cartridge or the size of the cartridge, for example. The encoded portion of the cartridge may be a color code.

DETAILED DESCRIPTION

Figure 1:
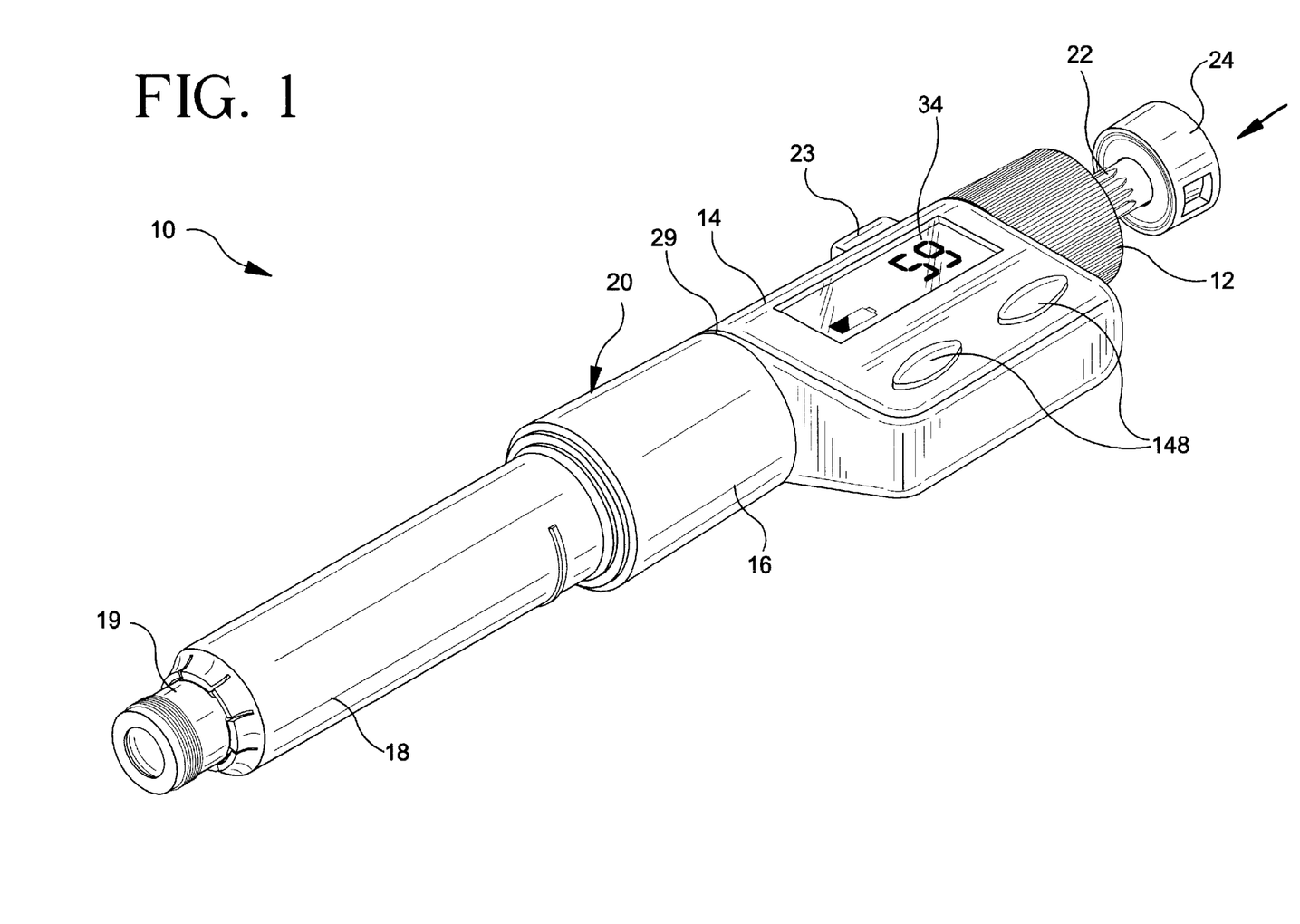
FIG. 1 is a perspective view of a medication delivery pen of the subject invention.

FIG. 1 shows a medication delivery pen in accordance with the present invention. The medication delivery pen includes a rotatable adjusting knob 12, a push button 24, an eject button 23, an upper body 14, a center body 16, and a medication cartridge retainer 18. Rotatable adjusting knob 12, eject button 23, and push button 24 are operatively coupled to a drive mechanism (see FIG. 2) located in upper and center bodies 14 and 16. Cartridge retainer 18 is adapted for receiving a medication cartridge of the type described below. The cartridge retainer 18 is coupled to an end of center body 16 so that the drive mechanism is operatively coupled to the medication cartridge.

Figure 2:
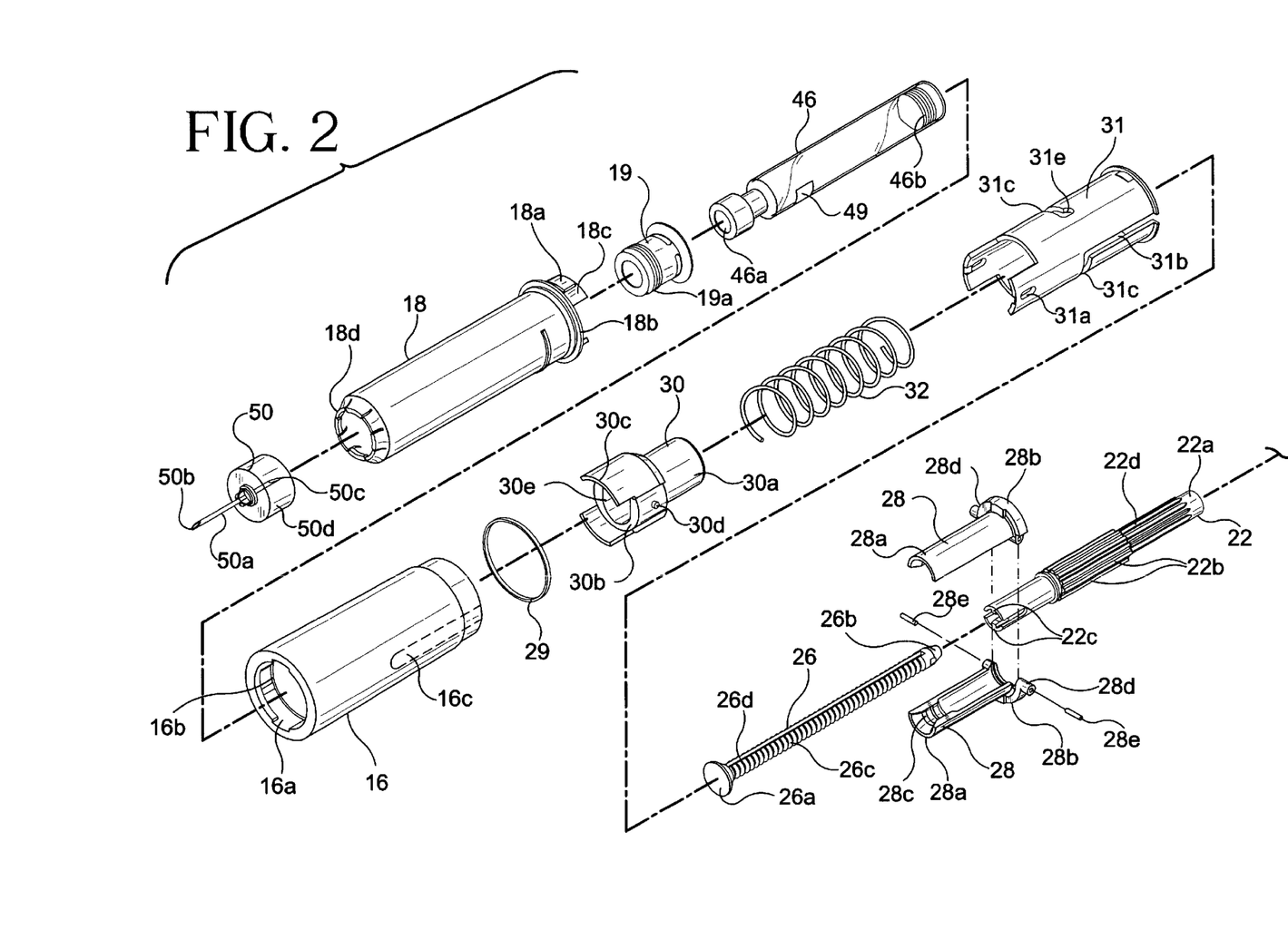
FIG. 2 is a an exploded perspective view of one embodiment of a drive mechanism that may be used in the pen shown in FIG. 1.

As shown in FIG. 2, cartridge retainer 18 is adapted for receiving a cartridge 46 of the type including an internal piston 46b and a pierceable seal 46a at one end thereof. An end cap 19 is inserted through cartridge retainer 18 to extend from a distal end of cartridge retainer 18. A needle assembly 50 is detachably coupled to end cap 19 by threads 19a, friction, or the like. Needle assembly is disposable so that the medication delivery pen can be used multiple times. In some cases only the needle 50b itself may be disposable.

When in the inject mode, the drive mechanism serves to translate the rotational displacement of adjusting knob 12 into a corresponding displacement of lead screw 26 via rotation of plunger 22 and half nuts 28. Push button 24 is then depressed a fixed distance so that the lead screw 26 contacts the piston 46b, displacing the piston 46b by a distance equal to the displacement of lead screw 26 so that fluid within cartridge 46 is forced through needle assembly 50. It should be noted that while FIG. 2 shows the details of one embodiment of a drive mechanism that may be employed in the present invention, this drive mechanism is shown for illustrative purposes only. More generally, the inventive medication delivery pen may employ many different types of drive mechanisms.

Figure 4:
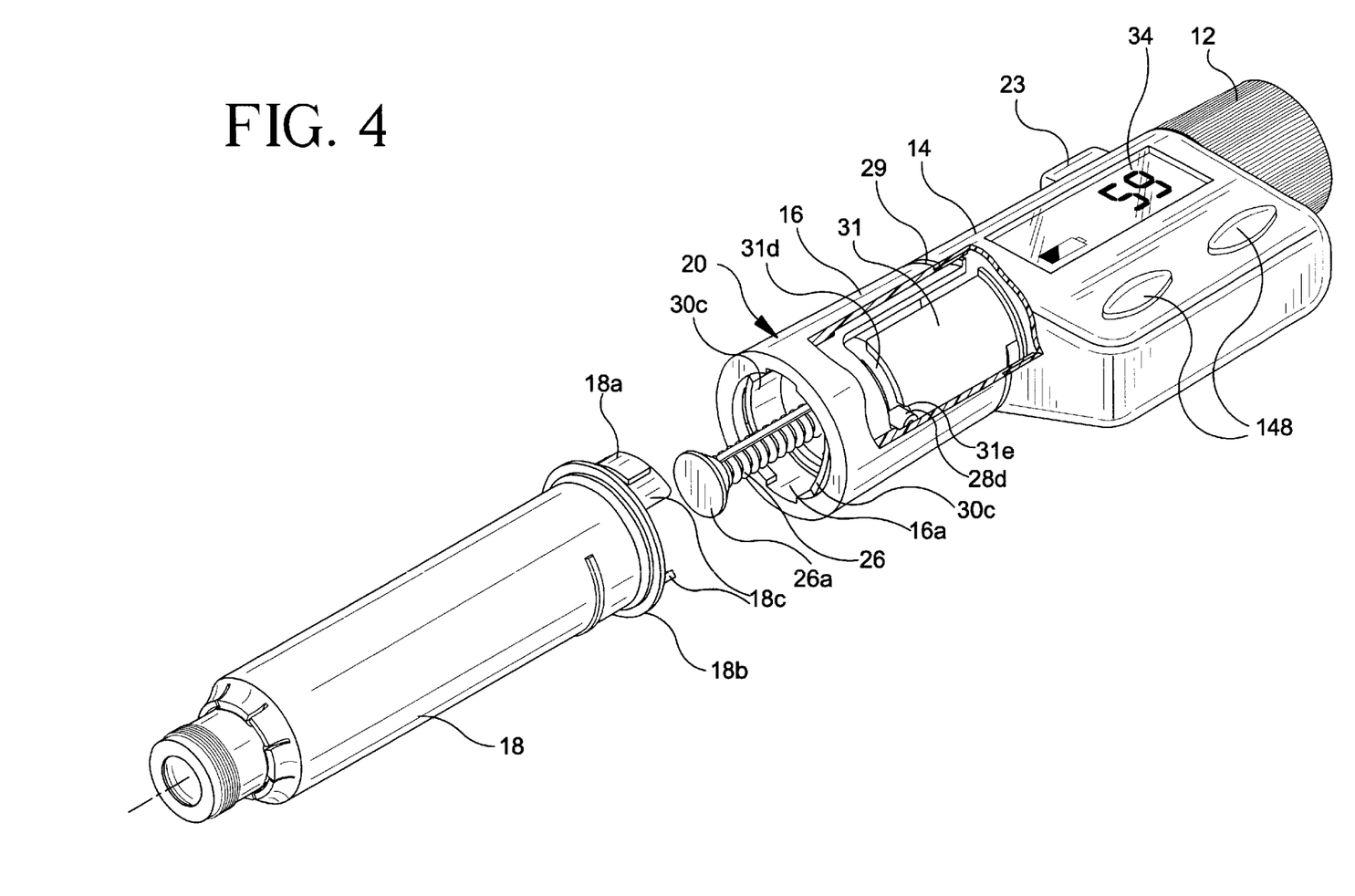
FIG. 4 is an exploded perspective view of the medication delivery pen shown in FIG. 1 with the cartridge retainer removed.
Figure 5:
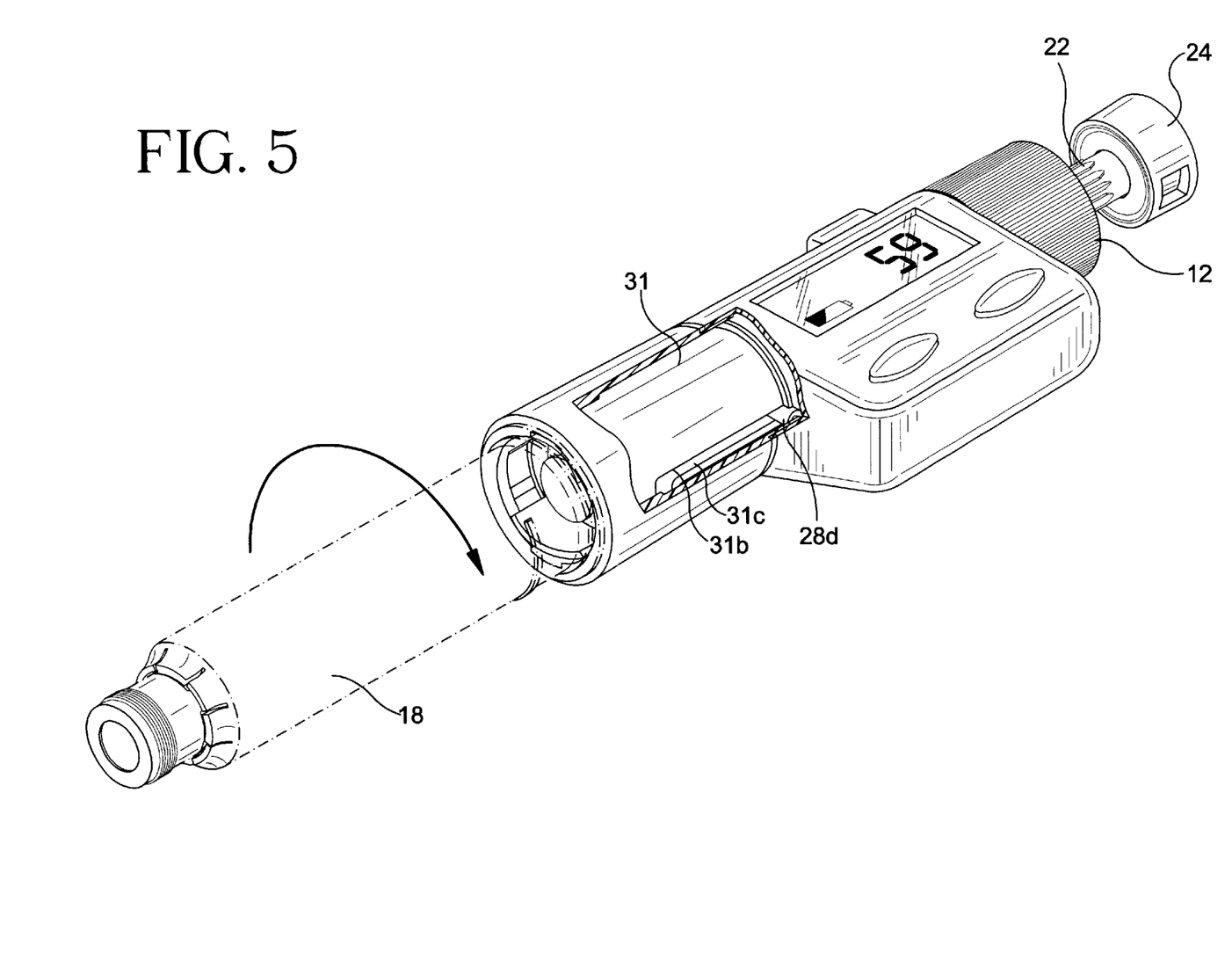
FIG. 5 is another perspective view of the medication delivery pen shown in FIG. 1 with the cartridge retainer attached and locked onto the upper body.

Referring again to FIGS. 2, and 3–5 a plunger 22 is at least partially positioned within the portion of housing 20 defined by adjusting knob 12, upper body 14 and center body 16. Plunger 22 includes a hollow, substantially cylindrical body 22a including a band of radially projecting splines 22b extending outwardly therefrom. A pair of opposing projections 22c extend radially inwardly from the distal end of the cylindrical body 22a. As shown in FIG. 5, the proximal end of plunger 22 is secured to a rotatable push button 24. Push button 24 fits within adjusting knob 12 when plunger 22 is fully inserted within housing 20.

A lead screw 26 is positioned within and coaxially with plunger 22 and includes an enlarged distal end 26a and a tapered proximal end 26b, connected by an elongate threaded body 26c. A pair of longitudinal grooves 26d are formed within threaded body 26c and receive the radially inwardly extending projections 22c of plunger 22. Lead screw 26 is accordingly rotatable with plunger 22 and capable of sliding axially with respect to plunger 22.

A pair of half-nuts 28 are positioned within center body 16, with each half-nut 28 including a semi-cylindrical body portion 28a and a radially enlarged end portion 28b. The distal end of each half-nut 28 includes threads 28c that are used to threadably engage with lead screw 26 and the proximal end of each half-nut 28 includes a pivot shaft 28d that receives a metal pin 28e to provide an axis about which each half-nut 28 can pivot. Metal pins 28e inserted in each pivot shaft 28d also provide more definite control over the dose setting operation, described below, and prevent skewing of half nuts 28 on threaded lead screw 26. Body portions 28a of half-nuts 28 are positioned at least partially within a locking ring 30 having a hollow, generally cylindrical body portion 30a defining a generally elliptical passage 30e for receiving half-nuts 28. A distal end 30b of locking ring 30 is radially enlarged and includes a pair of angular projections 30c that extend axially from the distal end of locking ring 30 and the side of locking ring 30 includes a pair of pins 30d. The proximal end 18b of cartridge retainer 18 includes a pair of angular projections 18c that are spaced to receive angular projections 30c when cartridge retainer 18 is mounted on housing 20, which is described further below.

A helical coil spring 32 is positioned over locking ring 30 and half-nuts 28 and through locking sleeve 31, with one end of coil spring 32 bearing against the radially enlarged portions 28b of half-nuts 28 while the opposite end of coil spring 32 bears against the radially enlarged distal end 30b of locking ring 30. Distal end 30b of locking ring 30 mounts within center body 16 which also receives finishing ring 29. The proximal end portion 28b of half-nuts 28 abut splines 22b of plunger 22.

Locking ring 30 is slidably mounted within locking sleeve 31 such that the pair of pins 30d on locking ring 30 are mounted and travel within slot 31a at a distal end of locking sleeve 31. With this structure locking ring 30 is axially movable within locking sleeve 31 but rotates with locking sleeve 31. Locking sleeve 31 also includes a pair of L-shaped grooves 31b that slidably receive each of the shafts 28d on half-nuts 28. Each pivot shaft 28d in conjunction with its respective L-shaped groove 31b on locking sleeve 31 and a long groove 16c within center body 16 provides a mechanism that prevents the removal of cartridge retainer 18 and cartridge 46 from housing 20, unless injector button 24 is in a down or loading position. This feature is more clearly shown in FIGS. 4 and 5. In FIG. 4 injector button 24 is in the down or loading position and device 10 is in the proper position for receiving cartridge retainer 18 and, in particular, lugs 18a can enter slot 16a of center body 16. As shown in FIG. 4, locking ring 30 is oriented so that tabs 30c do not block access to slot 16a and in this orientation pivot shafts 28d of half-nuts 28 are located in notches 31e at the end of each lower leg 31d of L-shaped groove 31b. After a cartridge 46 has been loaded into cartridge retainer 18, cartridge retainer 18 is mated with center housing 16 such that lugs 18a enter slot 16a. Then, as shown in FIG. 5, cartridge retainer 18 is rotated in a clockwise direction such that lugs 18a drive tabs 30c in a clockwise direction which moves locking sleeve 31 and causes pivot shaft 28d to slide out of each notch 3e and into each leg 31d of each L-shaped groove 31b. At this point, spring 32 drives half-nuts 28 in the proximal direction to extend injector button 24 from the proximal end of assembly 10, if the eject button 23 is depressed.

Figure 6:
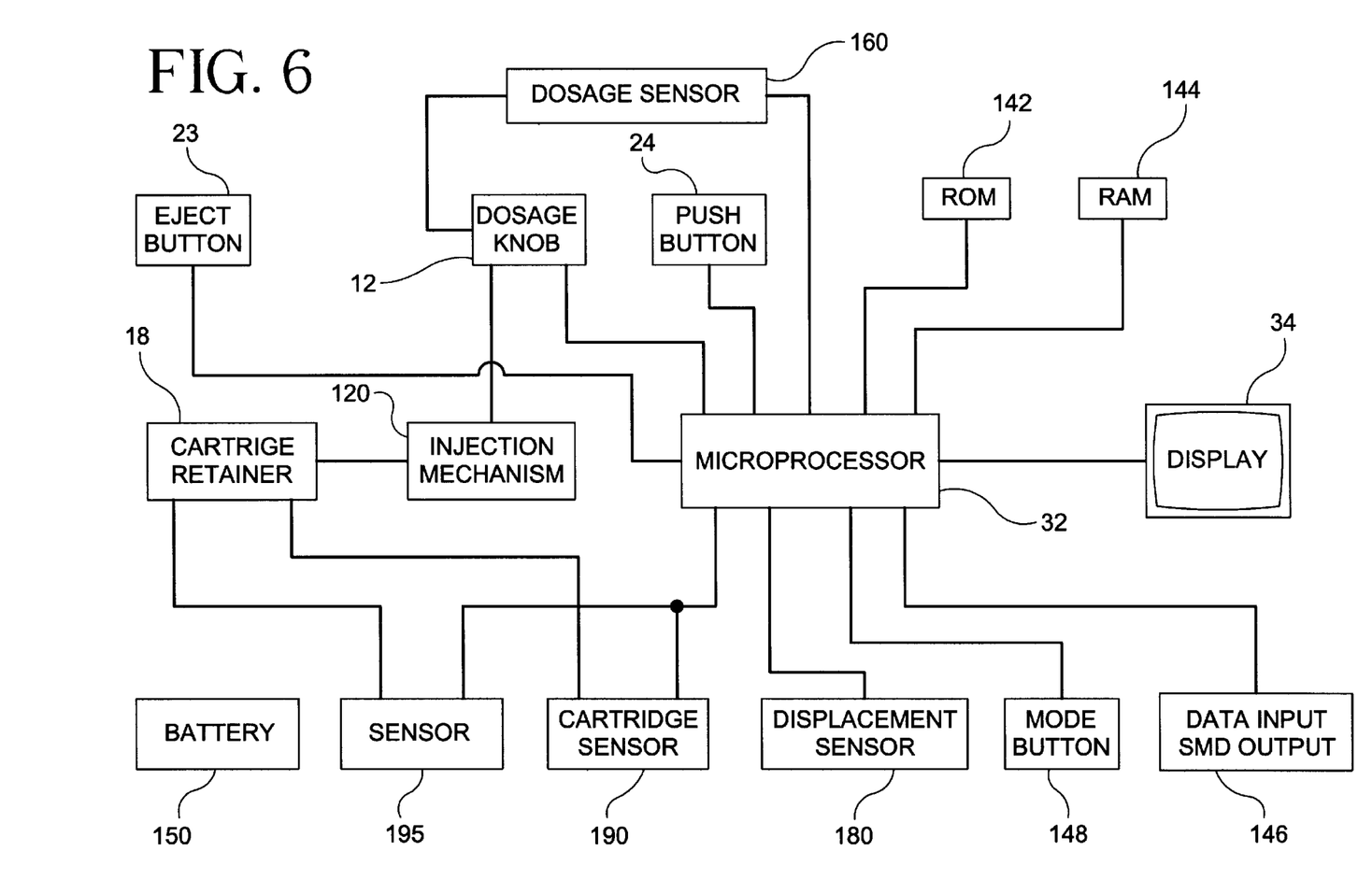
FIG. 6 is a simplified block diagram of the medication delivery pen shown in FIG. 1 showing the electrical communication paths between components.

Referring to FIG. 6, a microprocessor 32 is located in upper body 14. The microprocessor 32 determines the dosage of medication to be injected based upon the number of rotations of adjusting knob 12 as determined by a dosage sensor 160. Dosage sensor 160 may be any appropriate mechanism for determining the number of rotations, whether complete or incremental, that adjusting knob 12 undergoes in setting the dosage. Dosage sensor 160 may employ optical, magnetic, piezoelectric, or other means. For example, dosage sensor 160 may be an optical encoder in which an encoder disk is splined to the plunger 22 so that the plunger 22 is rotationally splined but axially free to travel within the disk. As the adjusting knob 12 is rotated, the plunger 22 rotates, which in turn rotates the encoder disk, whose rotational motion is detected by an optical receiver. The number of rotations of the encoder disk is translated into a dosage amount by the microprocessor 32. The microprocessor 32 provides the dosage information to a display 34 such as an LCD display for indicating the amount of medication that will be injected. The display 34 may also indicate other information such as the time and date. This information may be input to microprocessor 32 via mode buttons accessible on housing 20.

The operation of the medication delivery pen is as follows. Cartridge 46 is loaded within cartridge retainer 18 and cartridge retainer 18 is attached to housing 20. The needle assembly 50 is then affixed to the end of cartridge 18. Fluid communication is accordingly established between the injection portion of needle assembly 50 and the interior of cartridge 46. In order to set the dosage, eject button 23 is depressed so that push button 24 is ejected into its extended position in preparation to inject the medication. Once the appropriate dosage is set via rotation of adjusting knob 12, push button 24 is depressed, causing the drive mechanism to exert a force upon piston 46b, which is movably positioned within cartridge 46. Piston 46b displaces fluid within cartridge 46, causing its injection into body tissue through needle assembly 50. Assuming the device is loaded and push button 24 is in the depressed position, three steps are followed in the injection procedure: press eject button 23, set the dose via adjusting knob 12, and make the injection.

More specifically, the injection procedure begins by first pressing eject button 23, which causes the display to be reset to zero and causes ejection of push button 24 so that the pen enters its injection mode. Adjusting knob 12 is then rotated away from the zero setting to set the desired dosage. The drive mechanism travels along the length of housing 20 a distance that is proportional to the dosage displayed on display 34. Once the desired dose has been set, push button 24 is pushed fully in, which pushes the drive mechanism forward so that the drive mechanism performs the function of a piston rod so that the correct amount of medication in cartridge 46 is discharged through needle assembly 50.

Figure 3:
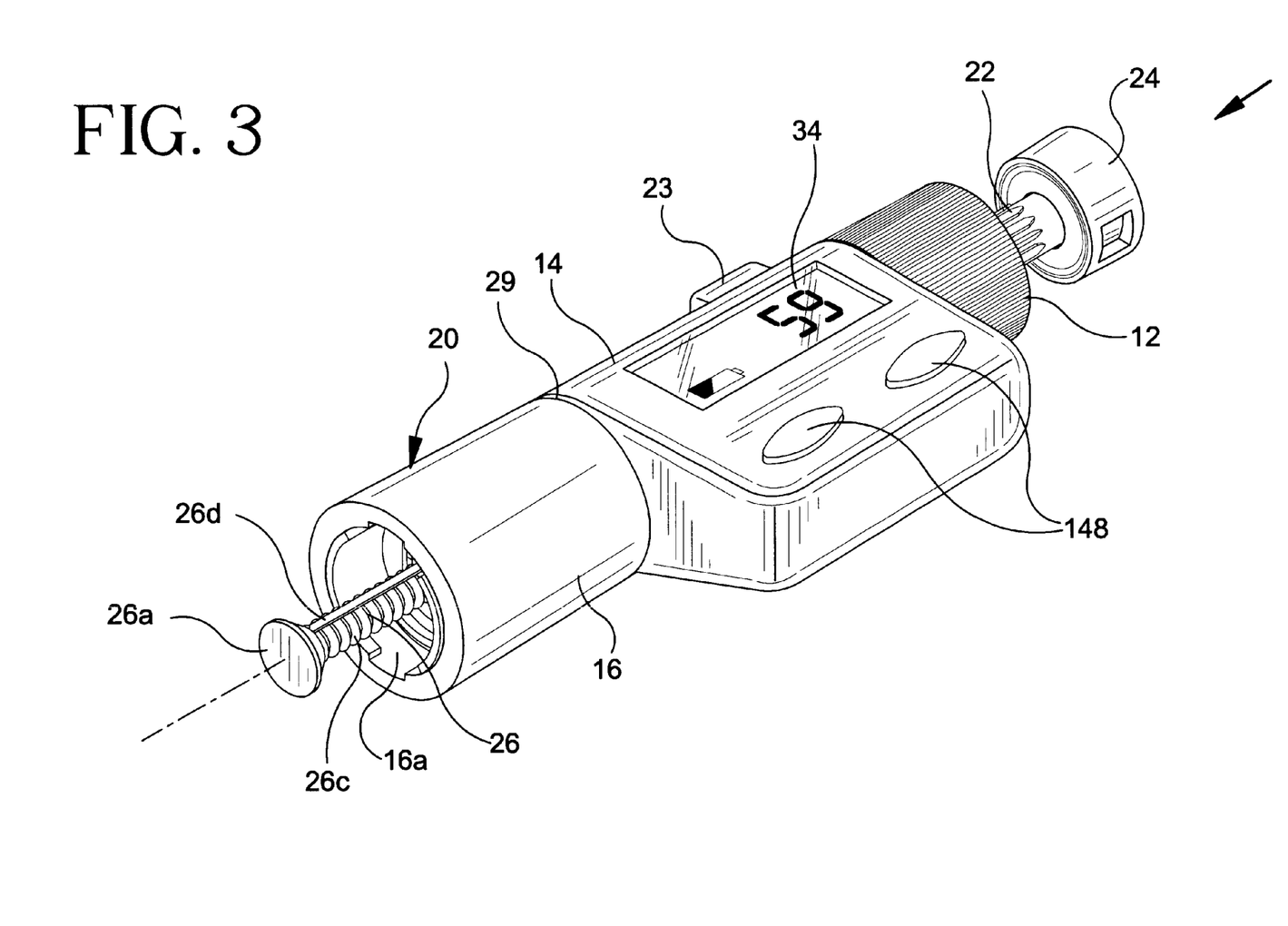
FIG. 3 is a perspective view of the medication delivery pen shown in FIG. I with the cartridge retainer removed.

FIG. 6 shows a simplified block diagram of the medication delivery pen shown in FIGS. 1–3. which illustrates the communication paths between the various elements of the pen. As previously mentioned, adjusting knob 12 is rotated to set the dosage and dosage sensor 160 measures the number of rotations (including partial rotations) of adjusting knob 12. Dosage sensor 160 is coupled to microprocessor 32, which keeps track of the accumulated rotations of actuator knob 12. Microprocessor 32 converts the accumulated number of rotations into a dosage value that is to be administered. Microprocessor 32 is coupled to memory storage components such as ROM 142 and RAM 144. The ROM 142 electronically stores the programs employed by microprocessor 32 to determine the dosage based on the accumulated number of rotations of adjusting knob 12. ROM 142 can also store additional programs that relate to other functions performed by microprocessor 32 such as the selection from among various display formats for displaying data on display 34. The RAM 144 stores information about the injection such as the dosage, time, and date so that these parameters may be subsequently recalled for display by the user or a medical practitioner. In some embodiments of the invention the information stored by RAM 144 may also be downloaded to an external device such as a computer through a data port 146. RAM 144 communicates with data port 146 via microprocessor 32. Data port 146 may be a bidirectional port for transferring data in both directions so that data such as revised programs, for example, can be uploaded to microprocessor 32. One or more mode buttons 148 located housing 20 allow the user to input information such as the time, date, and alarm settings and to select the desired display mode. A battery 150 such as a lithium battery, for example, supplies power to the previously mentioned electronic components.

Push button 24 and eject button 23 are each coupled to microprocessor 32 so that microprocessor 32 is activated when either of buttons 23 and 24 are depressed. When eject button 23 is depressed and push button 24 is in its ejected state, the pen enters its injection mode in preparation for the delivery of medication. When eject button 23 is in its ejected state and push button 24 is in its depressed state, the pen enters its non-injection mode. Since push button 24 is in its ejected state only when eject button 23 is in its depressed state, microprocessor 32 will cause an error message to be displayed on display 34 if it detects that both push button 24 and eject button 23 are in their depressed states. As previously discussed, in the non-injection mode push button 24 is disengaged from the drive mechanism. That is, when the pen is in its non-injection mode (e.g., when push button 24 is in its depressed state), rotation of adjusting knob 12 does not cause any displacement of the lead screw such as lead screw 26 shown in FIG. 2. Accordingly, the rotational state of adjusting knob 12 is now available to perform other functions. Upon detecting that the pen is in its non-injection mode, microprocessor 32 is available to perform other functions in accordance with the current operational mode of the pen. Similarly, upon detecting that the pen is in its inject mode, microprocessor 32 operates to determine the dosage that is set by adjusting knob 12.

In accordance with the present invention, the rotational state of adjusting knob 12 when push button 24 is disengaged from the drive mechanism is employed to set and adjust the value of the current operational mode of the medication delivery pen. The operational mode of the pen is selected by the mode button or buttons 148. Specifically, repeated activation of mode button 148 directs microprocessor 32 to enter different modes such as a time, date and alarm mode. The given mode that is selected via mode button 148 is reflected by display 34. For example, in the time mode, the current time appears on display 34. Once in a given mode, adjusting knob 12 is rotated to change the setting of that mode. For example, in the time mode, adjusting knob 12 changes the time setting while in the alarm mode adjusting knob 12 changes the setting of the alarm or alarms.

As further indicated in FIG. 6, a displacement sensor 180 provides information about the status of the injection mechanism to microprocessor 32. For example, the displacement sensor 180 can be used to determine the linear displacement of the drive mechanism, which is related to the amount of insulin that has been delivered. Displacement sensor 180 may be located in the grooves 26 of lead screw 26. In the particular embodiment of the invention shown in FIG. 2, sensor 180 determines the linear displacement of lead screw 26. As previously mentioned, the linear displacement of lead screw 26 is equal to the linear displacement of piston 46b in cartridge 46. The displacement of lead screw 26 may be measured on an incremental basis or on an absolute scale. An absolute scale is preferred because the displacement is directly proportional to the amount of insulin that remains in the pen. Accordingly, by detecting the position of lead screw 26 and providing this information to microprocessor 32, the amount of deliverable medication that remains in cartridge 46 can be displayed on display 34.

Displacement sensor 180 may be any appropriate mechanism that can determine the linear position of lead screw 26 at any given time. For example, similar to dosage sensor 160, displacement sensor 180 may employ optical, magnetic, or other means.

As further indicated in FIG. 6, a cartridge sensor 190 coupled to microprocessor 32 is employed to identify the type of cartridge 46 that is inserted into the cartridge retainer 18. The cartridge 46 may be identified by a color code that is provided on the cartridge 46. For example, if the pen is to be employed to deliver insulin, different insulin cartridges may be coded in accordance with the standard proposed by the International Diabetes Federation. This proposed standard assigns a unique color code to each different preparation of insulin, regardless of manufacturer. By providing the pen with the capability to detect the type of insulin or other medication that is installed in the cartridge retainer 18, the operation of the device is simplified from the user's perspective. Additionally, the likelihood of user error arising from inadvertently inputting incorrect information into the pen is substantially reduced.

Figure 7:
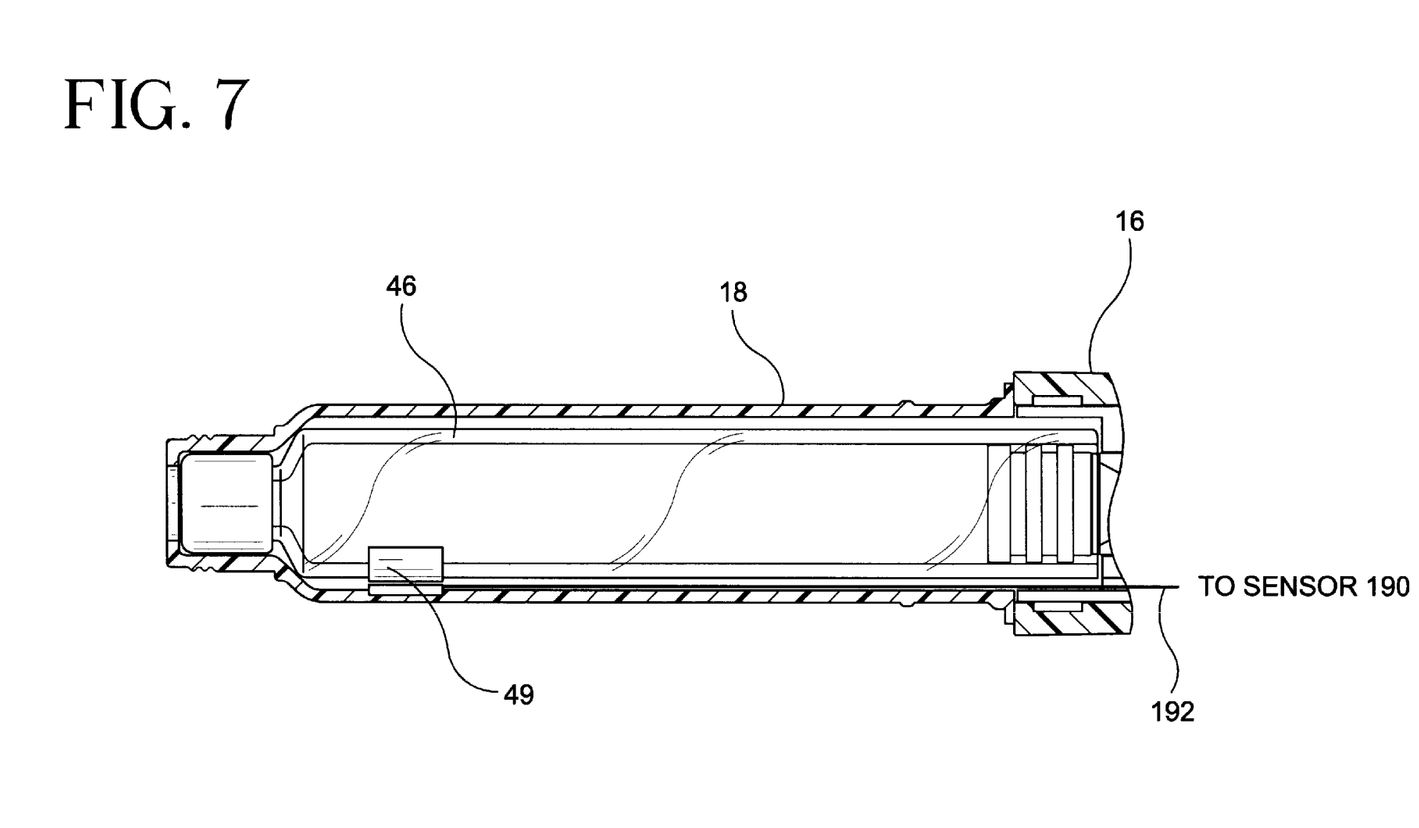
FIG. 7 shows a simplified diagram of a medication cartridge located in the cartridge retainer in which the cartridge includes a color code that is detected by a sensor via a light pipe or light guide situated in the cartridge retainer.

Cartridge sensor 190 may be located in cartridge retainer 18 so that it receives light directly from the color code on cartridge 46. Alternatively, cartridge sensor 190, which may be a photodetector, for example, may be provided on the same pc-board as the microprocessor 32 and other electronic components. In this case, as indicated in FIG. 7, the cartridge sensor 190 is connected to a light pipe or light guide 192 that is located in cartridge retainer 18. The light pipe or light guide terminates at a position to receive light reflected from the color code 49 on the cartridge 46. The light pipe or light guide 192 may be molded directly into cartridge retainer 18, and in the case of a light pipe, may comprise a series of exposed facets of cartridge retainer 18 itself, which are oriented to transfer the light reflected from the color code 49 to the cartridge sensor 190. The light reflected from the cartridge 46 and directed to cartridge sensor 190 may be ambient light or light that is provided by cartridge sensor 190 via the light pipe or light guide 192. The use of ambient light is preferable, however, to minimize power consumption.

In some embodiments of the invention the color code may be provided at a plurality of locations on cartridge 46. In this case a corresponding number of cartridge sensors may be employed to detect the plurality of codes. This arrangement advantageously reduces the likelihood of decoding errors since the processor will only identify the cartridge if a majority (or all) of the sensors are in agreement. If the sensors are not in agreement, an error condition will be indicated on display 34. The sensors may be configured so that their maximum sensitivity is located at a common wavelength, or alternatively, at different wavelengths.

Medication cartridges are often available in different sizes. For example, insulin cartridges are currently available in 1.5 and 3.0 ml sizes. Conventional medication delivery pens can only accept a single cartridge size, however. One problem in providing a pen that accommodates multiple cartridge sizes is that the ratio between the number of units of medication delivered and the linear displacement of the piston in the cartridge is different for each size cartridge. The present invention overcomes this problem by providing, in some embodiments, a second cartridge sensor 195 may be located in cartridge retainer 18 to identify the size of the cartridge 46 that is inserted into the cartridge retainer 18. Sensor 195 may be similar in type to sensor 190 and may be positioned to detect, for example, the outer edge of the cartridge. Alternatively, sensor 195 may be a mechanical sensor or the like. Once the size of the cartridge has been determined, the microprocessor 32 can adjust the calibration accordingly so that the proper relationship between the total rotational displacement of the adjusting knob 12 and the linear displacement of the piston in the cartridge 46 is used in determining the actual dosage of medication that is delivered.

What is claimed is:

1. A medication delivery pen, comprising:
    a housing having opposing proximal and distal ends;
    an actuator disposed in the proximal end of the housing for setting and administering a dosage of medication;
    a medication-containing cartridge assembly having a cartridge with a pierceably sealed distal end, an open proximal end, and a piston in sliding fluid tight engagement within said cartridge, wherein the open proximal end is attachable to the distal end of the housing;
    a drive mechanism coupled between the actuator and the cartridge to exert an axial force on the piston to inject the set dosage of medication, wherein the actuator triggers the drive mechanism to administer the injection of medication held in the cartridge;
    a processor coupled to the actuator to determine a value equal to the dosage set by the actuator;
    a memory device coupled to the processor to store at least the dosage value determined by the processor;
    a display located on said housing and coupled to said processor for displaying information provided by said processor; and
    wherein in a first state said actuator engages with the drive mechanism to deliver the medication and in a second state is disengaged from the drive mechanism, said actuator in its second state serving as a user adjustable input for changing and setting mode parameters of at least one preselected mode of the pen.

2. The medication delivery pen of claim 1 wherein said actuator includes a rotatable knob for setting the dosage of medication, said rotatable knob serving as said user adjustable input when in said second state.

3. The medication delivery pen of claim 2 wherein said rotatable knob is rotatable in said second state for changing and setting a mode parameter.

4. The medication delivery pen of claim 3 further comprising a user-activatable mode button located on said housing and coupled to said processor for selecting said preselected mode of the pen from among a plurality of modes.

5. The medication delivery pen of claim 4 wherein said plurality of modes includes a time mode and a date mode.

6. The medication delivery pen of claim 3 further comprising an eject button for selectively alternating between said first and second states of the actuator.

7. The medication delivery pen of claim 1 wherein said cartridge has an encoded portion identifying at least one characteristic of said cartridge and further comprising at least a third sensor coupled to said processor for detecting said encoded portion, said processor determining said at least one characteristic from said encoded portion.

8. The medication delivery pen of claim 7 wherein said encoded portion is a color code.

9. The medication delivery pen of claim 8 further comprising a light pipe communicating light received from the encoded portion of the cartridge to the third sensor, said third sensor being located in proximity to the processor.

10. The medication delivery pen of claim 9 wherein said light pipe is integrally formed with said cartridge assembly.

11. The medication delivery pen of claim 8 further comprising a light guide communicating light received from the encoded portion of the cartridge to the third sensor, said third sensor being located in proximity to the processor.

12. The medication delivery pen of claim 7 wherein said at least one characteristic includes the type of medication contained in said cartridge.

13. The medication delivery pen of claim 7 wherein said at least one characteristic includes the size of said cartridge, said processor further determining the amount of medication to be delivered for a given linear displacement of said piston located in said cartridge.

14. The medication delivery pen of claim 7 wherein said at least one characteristic includes the type of medication contained in said cartridge or the size of said cartridge, said processor further determining the amount of medication to be delivered for a given linear displacement of said piston located in said cartridge.

15. The medication delivery pen of claim 1 wherein said drive mechanism includes a linearly displaceable leadscrew and said actuator includes a rotatable knob coupled to said leadscrew such that rotational displacement of said rotatable knob translates into a corresponding linear displacement of said leadscrew.

16. The medication delivery pen of claim 15 further comprising a first sensor coupled to said processor, said first sensor being configured to determine the rotational displacement of said rotational knob, said processor converting said rotational displacement into a dosage of medication to be delivered.

17. The medication delivery pen of claim 16 wherein said first sensor is an optical encoder.

18. The medication delivery pen of claim 1 further comprising a second sensor coupled to said processor for detecting status information pertaining to the drive mechanism to determine a quantity of medication remaining in the cartridge.

19. The medication delivery pen of claim 18 wherein said drive mechanism includes a linearly displaceable leadscrew having a linear position proportional to the quantity of medication remaining in the cartridge and wherein said status information includes the linear position of said leadscrew.

20. The medication delivery pen of claim 19 wherein said second sensor is an optical sensor.

* * * * *